United States Patent
Wenniger

(10) Patent No.: US 6,982,098 B1
(45) Date of Patent: Jan. 3, 2006

(54) NUTRITIONAL WEIGHT LOSS AGENT AND METHOD

(75) Inventor: Michael P. Wenniger, Tempe, AZ (US)

(73) Assignee: Fun Unlimited Inc., Phoenix, AZ (US)

(*) Notice: Subject to any disclaimer, the term of this patent is extended or adjusted under 35 U.S.C. 154(b) by 0 days.

(21) Appl. No.: 10/709,746

(22) Filed: May 26, 2004

Related U.S. Application Data

(60) Provisional application No. 60/474,458, filed on May 30, 2003.

(51) Int. Cl.
*A61K 35/78* (2006.01)

(52) U.S. Cl. ............... 424/725; 424/440; 562/444; 426/660

(58) Field of Classification Search ............. 424/725, 424/440; 562/444
See application file for complete search history.

(56) References Cited

U.S. PATENT DOCUMENTS

| 5,626,849 | A | | 5/1997 | Hastings et al. |
| 5,817,329 | A | * | 10/1998 | Gardiner |
| 5,968,544 | A | * | 10/1999 | Howard et al. |
| 6,413,545 | B1 | | 7/2002 | Alviar et al. |
| 6,491,540 | B1 | | 12/2002 | Barreca |
| 2002/0077233 | A1 | | 6/2002 | Oldani |
| 2002/0187204 | A1 | | 12/2002 | Alviar et al. |
| 2003/0086960 | A1 | | 5/2003 | Seielstad et al. |
| 2003/0103910 | A1 | | 6/2003 | Barreca |

FOREIGN PATENT DOCUMENTS

WO  WO 01/05356 A2 * 1/2001

* cited by examiner

*Primary Examiner*—Susan D. Coe
(74) *Attorney, Agent, or Firm*—Brooks Kushman P.C.

(57) ABSTRACT

The present invention relates to an agent that suppresses appetite and provides quick energy. According to at least one aspect of the present invention, a lollipop is provided that suppresses appetite and provides quick energy. The lollipop is made from a premixed herbal formula that is combined with a hard candy confection base. The herbal premixed formula includes the following active ingredients: Guarana PE 22%; CitriMax®; and L-Tyrosine. The herbal premix formula can also include Vitamin B6; and Vitamin B12 Cyanacobalamin. The premixed formula is added to a candy base that may include corn syrup, Maltodextrin, sugar, natural color and natural flavorings.

5 Claims, No Drawings

NUTRITIONAL WEIGHT LOSS AGENT AND METHOD

CROSS REFERENCE TO RELATED APPLICATIONS

This application claims the benefit of U.S. provisional application Ser. No. 60/474,458, filed May 30, 2003.

BACKGROUND OF INVENTION

1. Field of the Invention

The present invention generally relates to an agent having a combination of herbal supplements and a method that aids in weight loss and providing energy. In particular, the present invention relates to a confection having a combination of herbal supplements that aid in weight loss by satisfying a person's need to eat while suppressing appetite and providing a source of quick energy.

2. Background Art

Controlling one's weight is an important part of maintaining a person's health and well being. Weight control can be achieved through diet and exercise. While a regular program of exercise is recommended, many people find it difficult to start an exercise regimen and continue with the exercise regimen for an extended period of time. Regular exercise, while burning calories, can also increase a person's appetite.

The other part of the weight control process is to diet. Dieting may take the form of limiting food intake to a specific caloric amount, eating measured portions of a variety of food products, fasting, or limiting food intake to certain types of food while eliminating the intake of other types of food. While there are a multitude of different types of diet programs, most fail because people on a diet find it difficult to stay on the diet regimen when they are hungry. When a person is hungry, it is difficult to control their urge to eat which almost invariably leads to failure of the diet program.

People who are overweight and need to control their weight frequently like to eat snacks or candy between meals. A desire to snack or eat candy can be triggered because a person is hungry or can be a behavioral habit.

There is a need for an improved weight control program that does not require excessive exercise or dieting without addressing the physiological urge to eat and psychological needs of some people to eat snacks and candy. The present invention addresses the above problems. Furthermore, in at least one embodiment, the present invention satisfies the need for a confection that suppresses appetite and provides a source of quick energy.

SUMMARY OF INVENTION

The present invention provides an agent that suppresses appetite and provides quick energy. According to at least one aspect of the present invention, a lollipop is provided that suppresses appetite and provides quick energy. The lollipop is made from a premixed herbal formula that is combined with a hard candy confection base. The herbal premixed formula includes the following active ingredients: Guarana PE 22%; CitriMax®; and L-Tyrosine. The herbal premix formula can also include Vitamin B6; and Vitamin B12 Cyanacobalamin. The premixed formula is added to a candy base including corn syrup, Maltodextrin, and optionally sugar, natural color and natural flavorings. The agent comprises the premixed herbal formula. In addition to being provided as a lollipop or confection/hard candy, the agent could be provided in a water drink or shake-type drink. Additionally, the agent could be provided in pill or capsule form.

The present invention also provides a diet method wherein the agent is injested with a glass of water 30 minutes before eating breakfast, lunch, and dinner. In at least one aspect, a lollipop confection as described above is eaten with a glass of water 30 minutes before eating breakfast, lunch, and dinner. The diet also requires that certain foods be eaten as a part of each meal. For example, breakfast would include a well-balanced meal including fresh fruit. Lunch would be a balanced meal including protein, vegetables, and complex carbohydrates. Dinner would be a well-balanced meal including protein and vegetables. The diet method also includes avoiding carbohydrate consumption after dinner and a prohibition against eating within three hours before bedtime.

DETAILED DESCRIPTION

A herbal based appetite suppressant agent is provided. The agent comprises a premixed formula. In at least one aspect, a herbal based appetite suppressant confection is made in the form of a lollipop in accordance with the present invention. The lollipop is made by combining the premixed formula with a hard candy base. The nutritional appetite suppressant includes herbs that suppress the appetite and other nutritional supplements that provide an energy boost.

The premixed formula is provided below in the following table:

| CONSTITUENT | AS FORMULATED | ACCEPTABLE RANGES |
| --- | --- | --- |
| Guarana PE 22% | 440 mg | 220–660 mg |
| CitriMax ® | 200 mg | 100–400 mg |
| L-Tyrosine | 200 mg | 100–400 mg |

In at least one aspect, the premixed formula also comprises:

| CONSTITUENT | AS FORMULATED | ACCEPTABLE RANGES |
| --- | --- | --- |
| Vitamin B6 | 400 mcg | 300 mcg–2 mg |
| Vitamin B12 Cyanocobalamin | 0.600 mcg | 0.540 mcg–6.000 mg |

In yet another aspect, the premixed formula is mixed with a hard candy base comprising:

| CONSTITUENT | AS FORMULATED | ACCEPTABLE RANGES |
| --- | --- | --- |
| Corn syrup | 7 grams | 3 grams–15 grams |
| Maltodextrin | 160 mg | 120–200 mg |

The constituents of the formula are described more specifically below. Guarana is a herbal substance that contains Guaranine that is a chemical substance with similar characteristics to caffeine. Guarana has found to be a stimulant that is similar to coffee in that it may make a person more awake and suppress a person's appetite.

Guarana also is a diuretic and can cause higher blood pressure and increased heart rate. Guarana PE 22% is a powder extract having 22% caffeine.

CitriMax® is a trademark of Inter Health Company and is an all natural plant extract known as hydroxycitric acid, HCA, or *Garcinia Cambogiac*. CitriMax® is obtained from a tropical fruit which is a species of the citrus family called *Garcinia Cambogia*. CitriMax® is not a stimulant but is a substance that reduces appetite by making meals more filling.

L-Tyrosine is an amino acid that the body synthesizes from phenylalanine, another amino acid. Vitamin B6 is necessary for conversion of L-Tyrosine into neuro transmitters including L-Dopa, Dopamine, Norepinephrine and Epinephrine.

The other optional active ingredients, Vitamin B6 and Vitamin B12 Cyanocobalamin, are widely recognized vitamins. Vitamin B6 (Pyridoxine Hydrochloride) is an essential vitamin. Vitamin B6 is essential to physical and mental health and is widely recognized as an essential vitamin. Vitamin B12 is a co-factor for two co-enzymes.

The above premixed formula may be mixed with a standard hard candy confection base. For example, the hard candy confection base may include corn syrup, Maltodextrin, and optionally sugar, natural color, and natural flavorings. The premix is added to the hard candy base and mixed and heated to 360° F. The mixture is then poured into lollipop forming molds with a handle or stick inserted so that a convenient lollipop confection is provided.

In addition to suppressing appetite and increasing energy levels, the lollipops aid in burning fat and calories. The lollipops taste great and are convenient. A lollipop may be taken anywhere and requires no mixing or measuring. A lollipop can be conveniently eaten when a person has an urge to snack or eat conventional candy. The herbal supplements when consumed as a lollipop with water work quickly and are satisfying both physiologically and psychologically.

The present invention also provides a diet method wherein the agent is ingested with a glass of water 30 minutes before eating breakfast, lunch, and dinner. In at least one aspect, a lollipop confection as described above is eaten with a glass of water 30 minutes before eating breakfast, lunch, and dinner. The diet also requires that certain foods be eaten as a part of each meal. For example, breakfast would include a well-balanced meal including fresh fruit. Lunch would be a balanced meal including protein, vegetables, and complex carbohydrates. Dinner would be a well-balanced meal including protein and vegetables. The diet method also includes avoiding carbohydrate consumption after dinner and a prohibition against eating within three hours before bedtime.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A lollipop consisting essentially of:

| CONSTITUENT | RANGES |
| --- | --- |
| Guarana PE 22% | 220–660 mg |
| Hydroxycitric acid | 100–400 mg |
| L-Tyrosine | 100–400 mg |
| Vitamin B6 | 300 mcg–2 mg |
| Vitamin B12 Cyanocobalamin | 0.540 mcg–6.000 mg |
| Corn syrup | 3 grams–15 grams |
| Maltodextrin | 120–200 mg |

2. A lollipop consisting essentially of:

| CONSTITUENT | AMOUNT |
| --- | --- |
| Guarana PE 22% | 440 mg |
| Hydroxycitric acid | 200 mg |
| L-Tyrosine | 200 mg |
| Vitamin B6 | 400 mcg |
| Vitamin B12 Cyanocobalamin | 0.600 mcg |
| Corn syrup | 7 grams |
| Maltodextrin | 160 mg |

3. The lollipop of claim 2 wherein the components comprise a substantially homogeneous composition.

4. The lollipop of claim 1 wherein the lollipop consists of:

| CONSTITUENT | RANGES |
| --- | --- |
| Guarana PE 22% | 220–660 mg |
| Hydroxycitric acid | 100–400 mg |
| L-Tyrosine | 100–400 mg |
| Vitamin B6 | 300 mcg–2 mg |
| Vitamin B12 Cyanocobalamin | 0.540 mcg–6.000 mg |
| Corn syrup | 3 grams–15 grams |
| Maltodextrin | 120–200 mg |

5. The lollipop of claim 2 wherein the lollipop consists of:

| CONSTITUENT | AMOUNT |
| --- | --- |
| Guarana PE 22% | 440 mg |
| Hydroxycitric acid | 200 mg |
| L-Tyrosine | 200 mg |
| Vitamin B6 | 400 mcg |
| Vitamin B12 Cyanocobalamin | 0.600 mcg |
| Corn syrup | 7 grams |
| Maltodextrin | 160 mg |

\* \* \* \* \*